(12) United States Patent
Liao et al.

(10) Patent No.: US 10,750,265 B1
(45) Date of Patent: Aug. 18, 2020

(54) SMART SPEAKER WITH FRAGRANCE DISPENSER

(71) Applicant: ELITEGROUP COMPUTER SYSTEMS CO., LTD., Taipei (TW)

(72) Inventors: Fang-Yang Liao, Taipei (TW); Kai-Chuan Hsieh, Taipei (TW); Yin-Hao Chang, Taipei (TW)

(73) Assignee: Elitegroup Computer Systems Co., Ltd., Taipei (TW)

( * ) Notice: Subject to any disclaimer, the term of this patent is extended or adjusted under 35 U.S.C. 154(b) by 0 days.

(21) Appl. No.: 16/556,859

(22) Filed: Aug. 30, 2019

(51) Int. Cl.
*H04R 1/02* (2006.01)
*H04R 3/00* (2006.01)
(Continued)

(52) U.S. Cl.
CPC ............ *H04R 1/028* (2013.01); *A61L 9/145* (2013.01); *H04R 1/025* (2013.01); *H04R 3/00* (2013.01);
(Continued)

(58) Field of Classification Search
CPC .......... H04R 1/028; H04R 9/046; H04R 9/06; H04R 1/1008; H04R 1/1016; H04R 1/1058; H04R 1/1091; H04R 2225/025; H04R 2225/61; H04R 2420/01; H04R 2420/05; H04R 2460/05; H04R 25/30; H04R 25/554; H04R 25/558; H04R 25/70; H04R 29/001; H04R 3/00; H04R 3/12; H04R 5/02; H04R 5/04; H04R 7/02; H04R 9/02; H04W 4/38; H04W 4/021; H04W 24/08; H04W 4/023; H04W 4/027; H04W 4/029; H04W 4/80; H04W 4/90; H04W 88/02; H04L 29/08; H04L 67/12; H04L 65/1063; H04L 65/4069; H04L 65/602; H04L 12/2829; H04L 2012/2841; H04L 65/4084; H04L 69/24; H04S 7/308; H04N 9/3147; H04N 9/3182; H04N 9/3194; H04N 21/4122; H04N 5/44591; H04N 9/3185; H04N 13/194; H04N 21/4131; H04N 5/74; H04N 7/17318; H04N 9/3141; H04M 1/21;
(Continued)

(56) References Cited

U.S. PATENT DOCUMENTS

2005/0185392 A1* 8/2005 Walter .................... A61L 9/145
362/96
2005/0195598 A1* 9/2005 Dancs ..................... A61L 9/037
362/231
(Continued)

*Primary Examiner* — Lun-See Lao
(74) *Attorney, Agent, or Firm* — Rosenberg, Klein & Lee

(57) ABSTRACT

The present invention provides a smart speaker with fragrance dispenser. A housing is disposed below a lid. One or more air outlet, one or more air inlet, and one or more sound outlet are disposed on one side of the housing. A fragrance module is disposed on the inner side of the housing for outputting fragrance. A speaker and the fragrance module are disposed separately. A dot-matrix display is disposed on one side of the speaker. The speaker outputs sound and the dot-matrix display outputs light. A processor is disposed below the speaker and connected electrically to the fragrance module, the speaker, and the dot-matrix display for controlling the output of fragrance, sound, and light. The present invention further adopts a limiting member so that the lid can rotate and slide on the fragrance module.

14 Claims, 7 Drawing Sheets

(51) Int. Cl.
*A61L 9/14* (2006.01)
*G09G 3/32* (2016.01)

(52) U.S. Cl.
CPC .......... *A61L 2209/132* (2013.01); *G09G 3/32* (2013.01); *H04R 2420/07* (2013.01); *H04R 2499/15* (2013.01)

(58) Field of Classification Search
CPC .. H04M 2250/12; H04M 1/67; H04M 1/7253; H04M 1/72569; H04M 11/066; H04M 19/04; H04M 1/0214; H04M 1/2535; H04M 1/57; H04M 1/72519; H04M 1/72536; H04M 1/72563; H04M 1/72597; H04M 3/20; H04M 3/42093; H04M 3/42348; H04M 3/42365; H04M 7/006
USPC ....... 381/332, 333, 312, 150, 337, 345, 352; 362/253
See application file for complete search history.

(56) References Cited

U.S. PATENT DOCUMENTS

| | | | | |
|---|---|---|---|---|
| 2006/0133215 A1* | 6/2006 | Gordon | ................. | G04G 11/00 |
| | | | | 368/79 |
| 2009/0108094 A1* | 4/2009 | Ivri | ........................ | A61L 9/127 |
| | | | | 239/101 |
| 2018/0369442 A1* | 12/2018 | Kelsen | .................... | H04W 4/38 |
| 2019/0236208 A1* | 8/2019 | Lee | .......................... | H04R 1/02 |

* cited by examiner

SMART SPEAKER WITH FRAGRANCE DISPENSER

FIELD OF THE INVENTION

The present invention relates generally to a smart speak with fragrance dispenser, and particularly to a device combining a smart speaker and a fragrance module.

BACKGROUND OF THE INVENTION

Thanks to the development of artificial intelligence, data technology, and network functions, various smart interactive devices are introduced in the industry. Take the smart speaker provided by Amazon in 2014 for example. A user needs to do nothing but speak then the smart speaker can execute the instructions of searching or making phone calls. Such kind of smart interactive devices facilitate intelligence of human lives and appeal to the industry. Companies also introduce smart interactive devices connected to their resources and advantages, along with various subsidies, promotion, and more advanced applications, for creating significant growth of the market.

The smart interactive device according to the prior art is generally a cylindrical structure mainly designed to be placed on a table or a cabinet in the living room. By means wireless transmission, the device, for example, a smart speaker, is connected to the cloud for searching the information required by users. As the technologies develop, the smart speaker is combined with the cloud for making phone calls, searching maps, network trading, receiving news, and turning on the connected appliance for users through the Internet.

Unfortunately, the smart speakers according to the prior art are mostly independent products integrating multiple network smart applications such as stream music, stream video, and network information services by individual companies. As large network and hardware companies join the competition of smart speakers, the smart applications broaden the competition scope such as integrated noise cancellation microphone array, AI voice recognition, AI scene analysis, and automatic applications. To increase the market growth of smart speakers, smart speakers combining with other devices are designed for attracting more consumers and customers.

According to the development of smart interactive device as described above, the present invention provides a device combining a smart speaker a fragrance dispenser. In the smart speaker, a fragrance module is combined with a speaker. The aroma and sound are used to enhance the sensation of a user's nose and ears and hence solving the problem of lacking a single structure integrating the two functions.

SUMMARY

An objective of the present invention is to provide a smart speaker with fragrance dispenser. A fragrance module, a speaker, a dot-matrix display, and a processor are disposed on the inner side of a housing. The processor controls the output of fragrance, sound, and light for providing a user's senses of smelling, hearing, and sight.

Another objective of the present invention is to provide a smart speaker with fragrance dispenser. A fragrance module, a speaker, and a processor are disposed on the inner side of a housing. The processor controls the output of fragrance and sound for providing a user's senses of smelling and hearing. In addition, a lid is disposed on the top of the housing and the fragrance module includes a magnetic member for avoiding foreign matters from entering the housing and for the convenience of replacing the internal devices in the housing.

To achieve the above objectives, the present invention provides a smart speaker with fragrance dispenser, which comprises a lid, a housing, a fragrance module, a speaker, a dot-matrix display, a processor, and a power device. One or more air outlet is disposed on one side of the housing. A sound receiving device is disposed on the top of the lid. The housing is disposed below the lid. One or more air inlet and one or more sound outlet are disposed on one side of the housing. A first opening and the sound receiving device are disposed on the top of the housing. The sound receiving device is located on the top of the first opening. The one or more air inlet is located on the top of the one or more sound outlet. The fragrance module is disposed on the inner side of the housing. The fragrance module includes an accommodating space, an ultrasonic oscillating device, and a fan. The accommodating space is located on one side of the one or more air outlet, includes a second opening and a channel, and is stacked on the first opening and communicating the one or more air outlet. One end of the channel is communicating the second opening. The ultrasonic oscillating device is communicating the bottom of the accommodating space. The fan is disposed below the ultrasonic oscillating device, communicating the other end of the channel, and located above the one or more air inlet. The speaker and the fragrance module are disposed separately and located on the inner side of the housing. The speaker is located below the one or more air inlet. The location of the speaker corresponds to the location of the one or more sound outlet. The dot-matrix display is located on one side of the speaker and located on the inner side of the housing. The processor is disposed below the speaker, located on the inner side of the housing, and connected electrically to the ultrasonic oscillating device, the fan, the speaker, the dot-matrix display, and the sound receiving device, respectively. The power device is disposed below the housing and connected electrically to the processor. The above structure combining the fragrance module, the speaker, and the processor is used for providing a user's senses of smelling, hearing, and sight.

To achieve the above objectives, the present invention provides a smart speaker with fragrance dispenser, which comprises a lid, a housing, a fragrance module, a speaker, a dot-matrix display, a processor, and a power device. One or more air outlet is disposed on one side of the housing. A sound receiving device is disposed on the top of the lid. A shaft and one or more magnetic member are disposed below the lid. The housing is disposed below the lid. One or more air inlet and one or more sound outlet are disposed on one side of the housing. A first opening is disposed on the top of the housing. The one or more air inlet is located on the top of the one or more sound outlet. The fragrance module is disposed below lid and on the inner side of the housing. The fragrance module includes an accommodating space, an ultrasonic oscillating device, and a fan. The accommodating space is located on one side of the one or more air outlet, includes a second opening and a channel, and is stacked on the first opening and communicating the one or more air outlet. One end of the channel is communicating the second opening. One or more second magnetic member is disposed on the top of the accommodating space corresponding to the one or more first magnetic member. The accommodating space includes a limiting member at the location corresponding to the shaft. The shaft is disposed slidably in the limiting member. The ultrasonic oscillating device is communicating the bottom of the accommodating space. The fan is disposed below the ultrasonic oscillating device and located above the one or more air inlet. The speaker and the fragrance module are disposed separately and located on the inner side of the housing. The speaker is located below the one or more air inlet. The location of the speaker corresponds to the location of the one or more sound outlet. The processor is disposed below the speaker and connected electrically to the ultrasonic oscillating device, the fan, the speaker, and the sound receiving device, respectively. The power device is disposed below the housing and connected electrically to the processor. The above structure is used for avoiding foreign matters from entering the housing and for the convenience of replacing the internal devices in the housing.

According to an embodiment of the present invention, the housing is a transparent member.

According to an embodiment of the present invention, the dot-matrix display is an LED matrix display.

According to an embodiment of the present invention, the fragrance module further includes a frame disposed between the accommodating space and the speaker. The ultrasonic oscillating device and the fan are located on the inner side of the frame.

According to an embodiment of the present invention, the processor is connected with a remote device for receiving a wireless signal from the remote device or transmitting a wireless signal to the remote device.

According to an embodiment of the present invention, the smart speaker with fragrance dispenser further comprises a power device disposed below the housing and connected electrically to the processor.

According to an embodiment of the present invention, the shaft is connected pivotally to the top of the accommodating space.

According to an embodiment of the present invention, the smart speaker with fragrance dispenser further comprises a touch device disposed on the top of the lid. The sound receiving device is disposed on the top of the touch device and connected electrically to the ultrasonic oscillating device and the fan.

DETAILED DESCRIPTION

In order to make the structure and characteristics as well as the effectiveness of the present invention to be further understood and recognized, the detailed description of the present invention is provided as follows along with embodiments and accompanying figures.

The present invention provides a smart speaker with fragrance dispenser. One or more air outlet is disposed on one side of a housing. One or more air inlet and one or more sound outlet are disposed on the same side of the housing. A fragrance module is disposed on the inner side of the housing for outputting fragrance. Then a speaker is disposed separately from the fragrance module and located on the inner side of the housing for outputting sound. A dot-matrix display outputs light. A processor is connected electrically to the fragrance module and the speaker for controlling the output of fragrance, sound, and light of the smart speaker with fragrance dispenser. A slidable lid is further disposed on the top of the housing for replacing internal devices and refilling liquid to the fragrance module.

Figure 1:
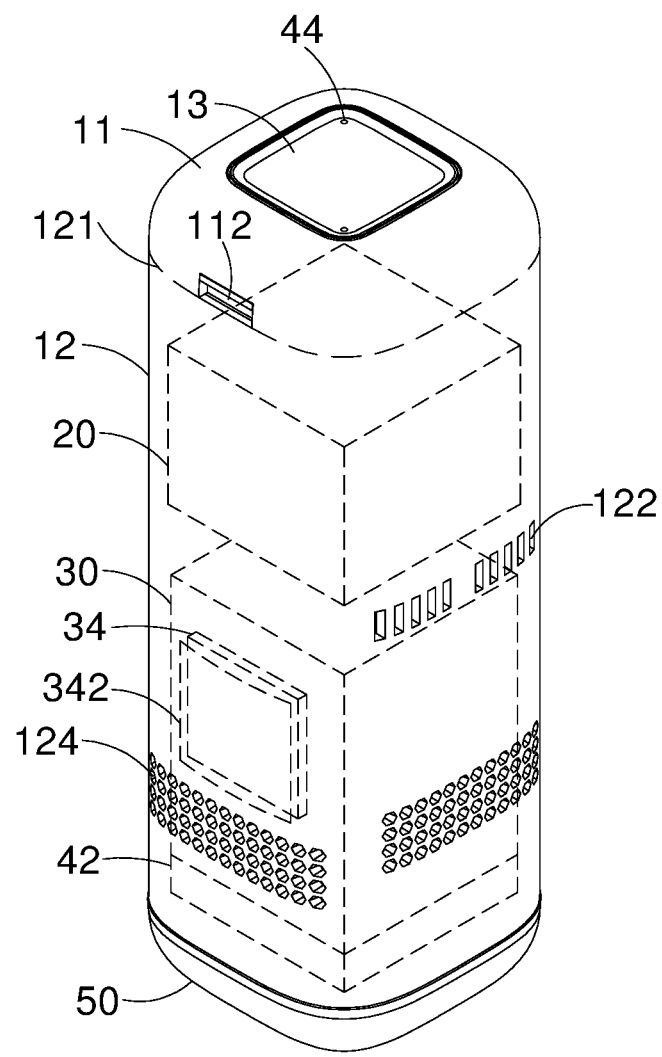
FIG. 1 shows a structural schematic diagram according to an embodiment of the present invention.

Please refer to FIG. 1, which shows a structural schematic diagram according to an embodiment of the present invention. As shown in the figure, according to a first embodiment of the present invention, the smart speaker with fragrance dispenser 1 comprises a lid 11, a housing 12, a fragrance module 20, a speaker 30, a dot-matrix display 34, and a processor 42. The lid 11 is disposed on (covering) the top of the housing 12. The fragrance module 20, the speaker 30, the dot-matrix display 34, and the processor 42 are disposed on the inner side of the housing 12 (for example, inside the housing 12). Besides, the fragrance module 20 is located on the speaker 30 and disposed separately. The processor 42 is disposed below the speaker 30 for controlling the fragrance module 20 and the speaker 30.

Figure 2:
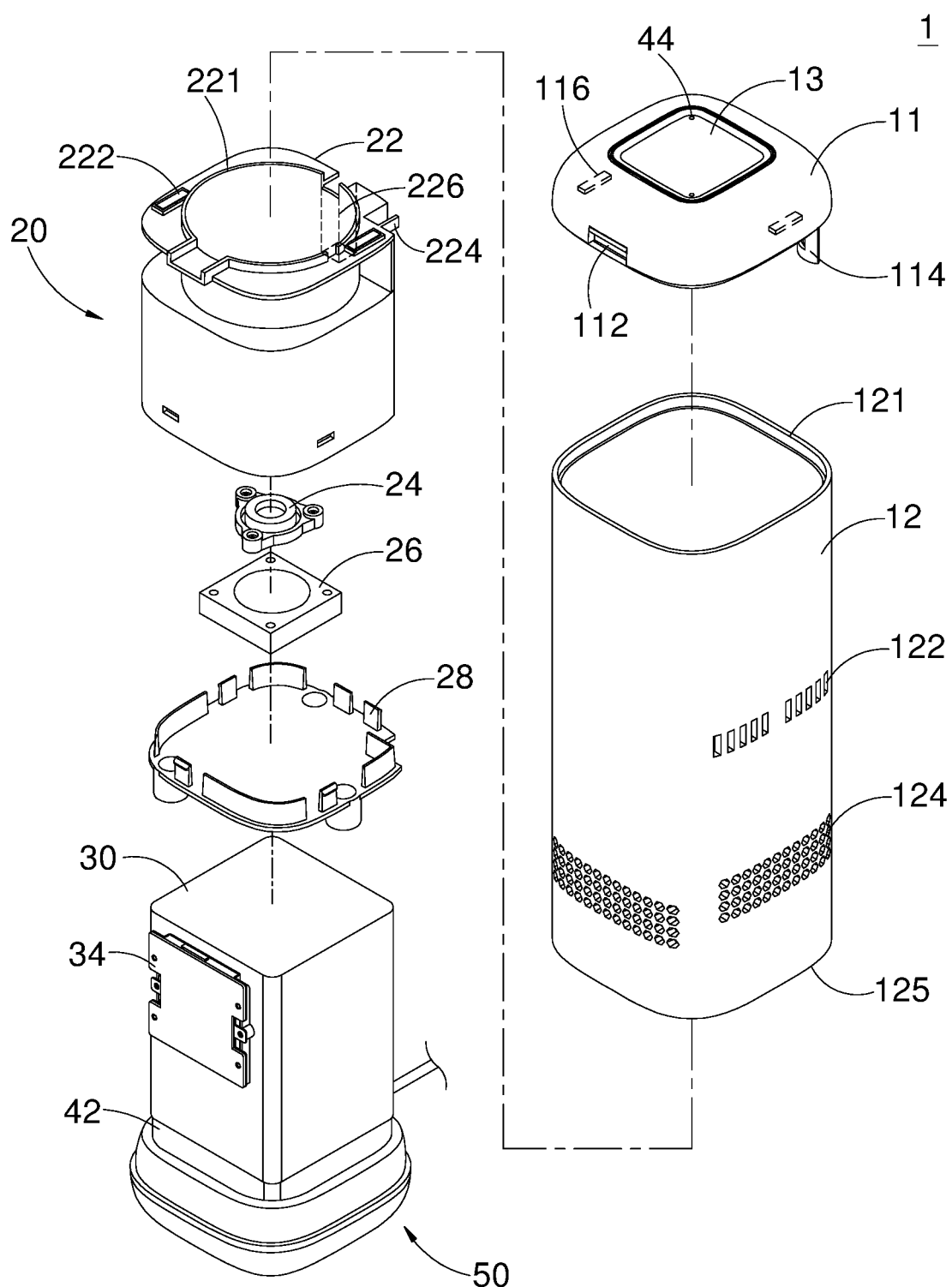
FIG. 2 shows an exploded view according to an embodiment of the present invention.

Please refer to FIG. 1 again and to FIG. 2, which shows an exploded view according to an embodiment of the present invention. As shown in the figures, one or more air outlet 112 is disposed on one side of the lid 11 for outputting nebulized liquid and air. A sound receiving device 44 is disposed on the top of the lid 11. The housing 12 is disposed below the lid 11. One or more air inlet 122 and one or more sound outlet 124 are disposed on one side of the housing 12. The one or more air inlet 122 allows air to enter. A first opening 121 is disposed on the top of the housing 12. The one or more air inlet 122 is located on the top of the one or more sound outlet 124. The fragrance module 20 includes an accommodating space 22, an ultrasonic oscillating device 24, and a fan 26. The accommodating space 22 is located on one side of the one or more air outlet 122, includes a second opening 221 and a channel 226, and is stacked on the first opening 121. The second opening 221 is communicating the one or more air outlet 112. One end of the channel 226 is communicating the second opening 221. The accommodating space 22 provides space for accommodating liquid. The ultrasonic oscillating device 24 is communicating the bottom of the accommodating space 22. The fan 26 is disposed below the ultrasonic oscillating device 24 and located above the one or more air inlet 122 for inhaling air into the one or more air inlet 122. The speaker 30 and the fragrance module 20 are disposed separately and located on the inner side of the housing 12. The speaker 30 is located below the one or more air inlet 122. The location of the speaker 30 corresponds to the location of the one or more sound outlet 124 for outputting sound to the one or more sound outlet 124 and avoiding obstruction of sound by internal devices. The dot-matrix display 34 is located on one side of the speaker 30 and corresponding to a light-emitting region 342 of the housing 12. According to a preferred embodiment, the housing 12 is a transparent member. Particularly, only the light-emitting region 342 is transparent. The processor 42 is disposed below the speaker 30, located on the inner side of the housing 12, and connected electrically to the ultrasonic oscillating device 24, the fan 26, the speaker 30, the dot-matrix display 34, and the sound receiving device 44, respectively. The processor 42 turning on and off the ultrasonic oscillating device 24 and the fan 26 for controlling the fragrance output of the fragrance module 20. The processor 42 also controls the sound output of the speaker 30, as well as the light emission and displaying of the dot-matrix display 34.

According to the present embodiment, the fragrance module 20, the speaker 30, and the dot-matrix display 34 are disposed on the inner side of the housing 12. The fragrance module 20 provides fragrance variation; the speaker 30 provides sound variation; and the dot-matrix display 34 provides light variation. The processor 42 controls the fragrance, sound, and light outputs for enhancing a user's senses of smelling, hearing, and sight.

According to the present embodiment, the fragrance module 20 further includes a frame 28 disposed between the accommodating space 22 and the speaker 30 and located in the gap between the speaker 30 and the fragrance module 20. The frame 28 supports the accommodating space 22 and separates the housing 12. It also envelops the ultrasonic oscillating device 24 and the fan 26 and makes them be located in the inner side thereof.

According to the present embodiment, the gap between the speaker 30 and the fragrance module 20 corresponds to one or more air inlet 122 for allowing air to enter. The ultrasonic oscillating device 24, for example, an ultrasonic nebulizer, generates ultrasonic oscillation for nebulizing the liquid inside the accommodating space 22. The dot-matrix display 34 adopts an LED matrix display. Besides, a liquid-crystal panel can be used instead.

Figure 3A:
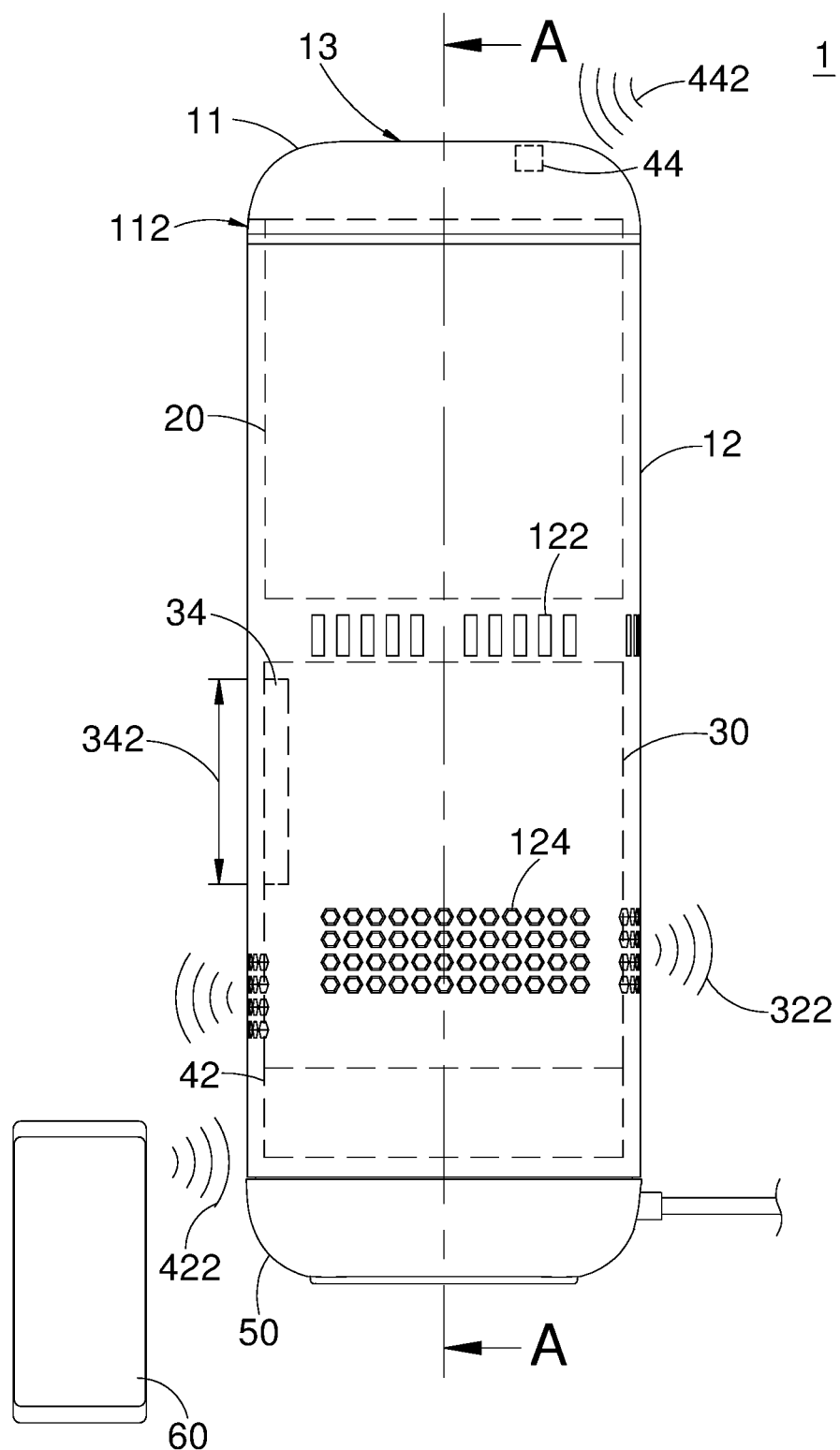
FIG. 3A shows a structural schematic diagram of the right side according to an embodiment of the present invention.
Figure 4:
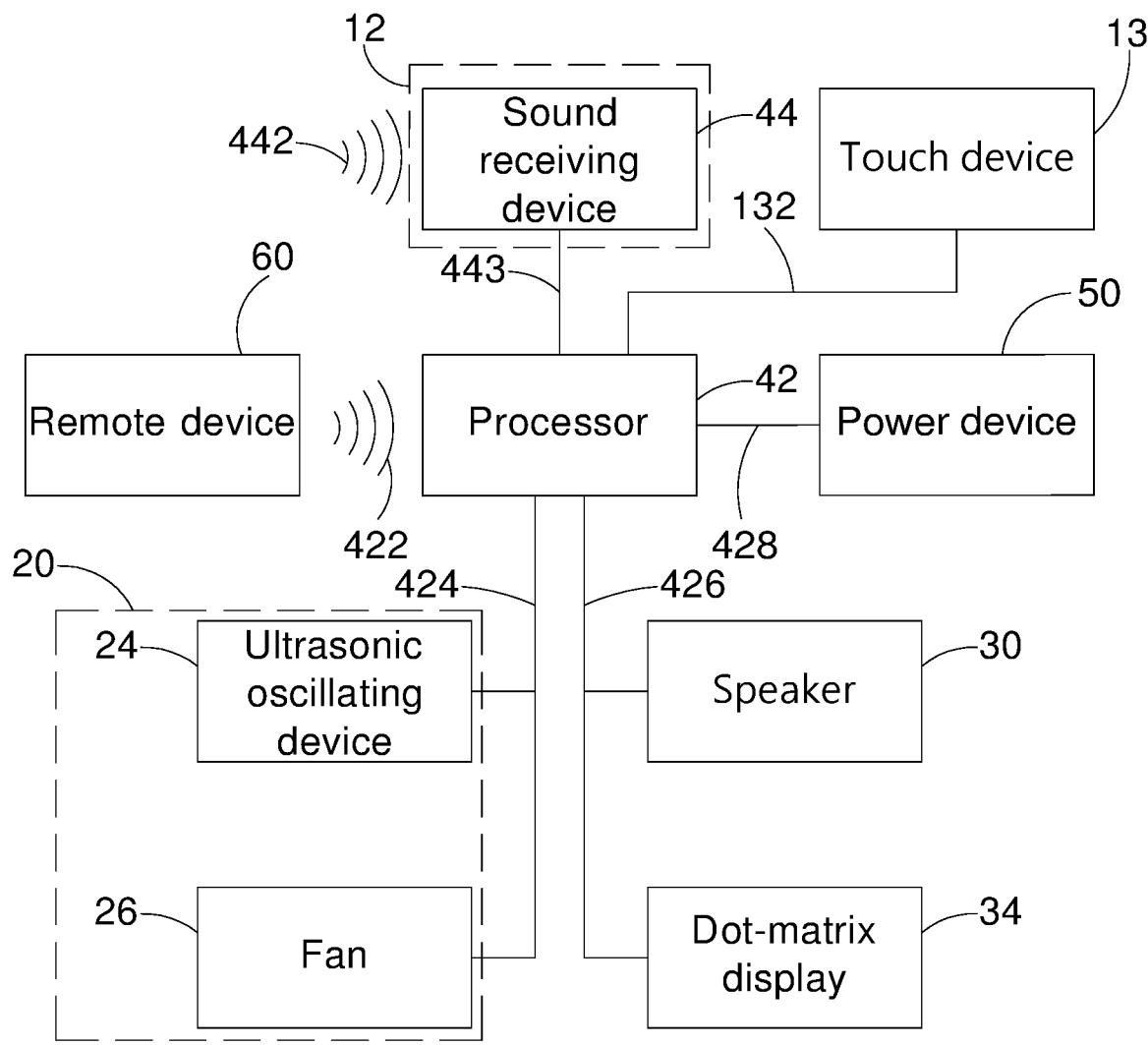
FIG. 4 shows a block diagram of signals according to an embodiment of the present invention.

Please refer to FIG. 3A and FIG. 4. FIG. 3A shows a structural schematic diagram of the right side according to an embodiment of the present invention; FIG. 4 shows a block diagram of signals according to an embodiment of the present invention. As shown in the figures, the speaker 30 generates and outputs a sound signal 322 to one or more sound outlet 124. The sound signal 322 can be music, alarm, or other sound. The dot-matrix display 34 generates and emits light to the light-emitting region 342 for displaying, for example, time, weather information, pattern variations, and the capacity of the liquid in the accommodating space 22. The processor 42 and connected with a remote device 60 and receives or transmits a wireless signal 422 of the remote device 442 for controlling fragrance, sound, and light remotely. The sound receiving device 44 receives a sound control signal such as the user's sound. Then the sound receiving device 44 converts the sound control signal 442 to a digital signal 443 and transmits the digital signal 443 to the processor 42. The processor 42 outputs a first control signal 424 to control fragrance, outputs a second control signal 426 to control the output of sound, and controls the output of light of the dot-matrix display 34 according to the digital signal 442. According to a preferred embodiment, the remote device 60 can be a smartphone or a personal computer. According to the present embodiment, the sound receiving device 44 is used to receive the sound signal 442 and the processor 42 is used to transmit the control signals 424, 426 for controlling the connected devices, such as voice controlling the speaker 30 to turn on, and voice controlling the dot-matrix display 34 to display time, weather, or news.

Figure 3B:
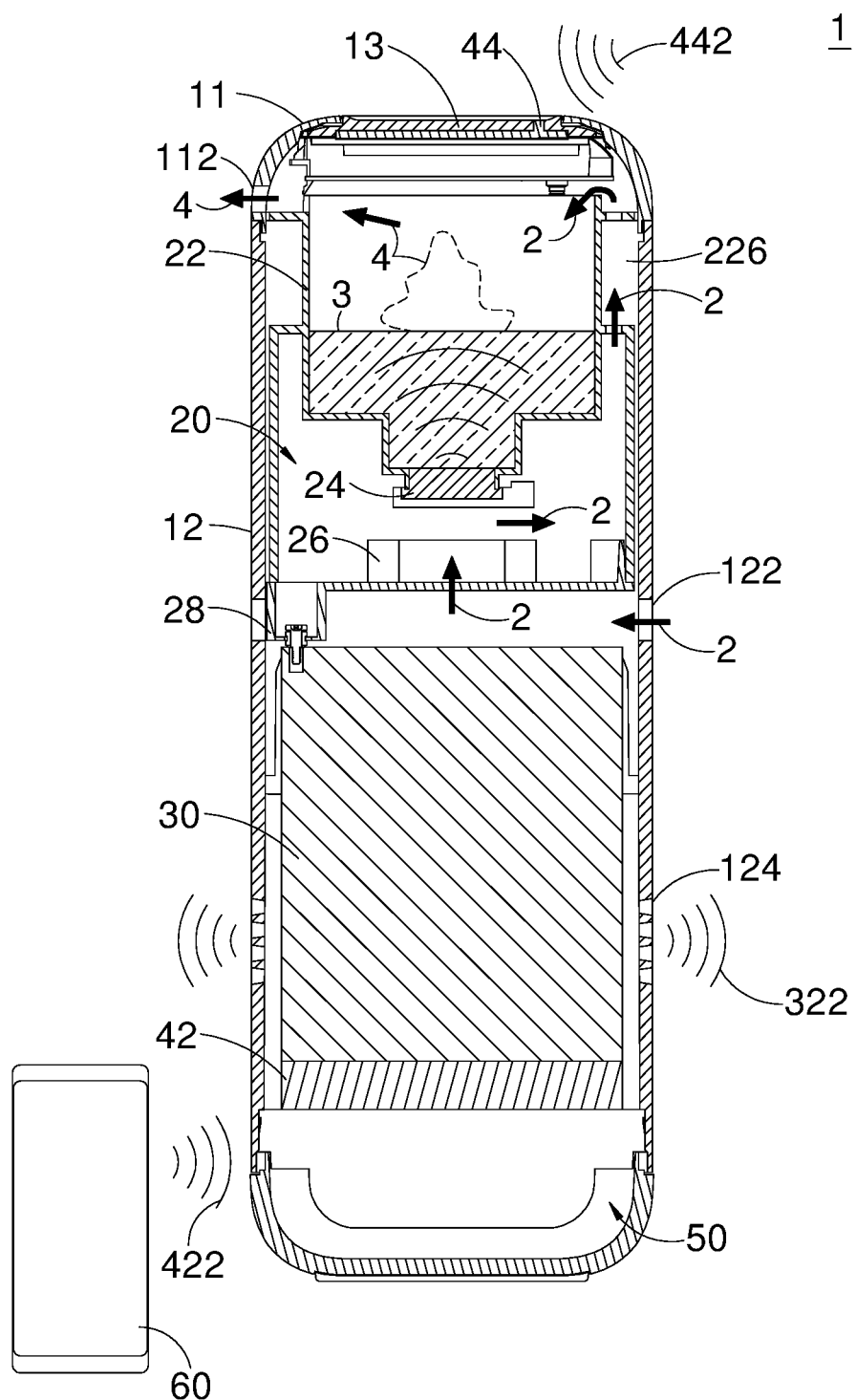
FIG. 3B shows a cross-sectional view according to an embodiment of the present invention.

Please refer to FIG. 3A again and to FIG. 3B, which shows a cross-sectional view according to an embodiment of the present invention and provides a cross-sectional view along A-A in FIG. 3A. As shown in the figures, the one or more air outlet 112 is communicating the accommodating space 22 of the fragrance module 20 for delivering the nebulized liquid 4 and air 2. A liquid 3 can be accommodated in the inner sider of the accommodating space 22. Under the influence of atmospheric pressure and gravity, the liquid 3 flows downward to the ultrasonic oscillating device 24. The ultrasonic oscillating device 24 generates ultrasonic oscillations. By using high-frequency oscillation waves, the liquid 3 is vibrated to mist particles and forming a nebulized liquid 4. Then the fan 26 inhales external air 2 from one or more air inlet 122 into the gap between the speaker 30 and the fragrance module 20 and to the channel 226. The air 2 is transported to the accommodating space 22 from the channel 226 and driving the nebulized liquid 4 be blown to the one or more air outlet 112. According to the present embodiment, the liquid 3 is the mixed liquid of flavoring essence and fragrance according to the prior art for providing fragrance variations. According a preferred embodiment, the processor 42 can integrate fragrance, sound, and light-emission display. For example, the dot-matrix display 34 varies according to the sound signal 322. Meanwhile, the fragrance module 20 delivers the nebulized liquid 4.

Please refer to FIGS. 1 to 4 again. As shown in the figures, the present embodiment further comprises a touch device 13, which is disposed on the lid 11, connected electrically to the processor 42, and outputs a first touch signal 132 to the processor 42. Then the processor 42 controls the ultrasonic oscillating device 24 and the fan 26 connected electrically to it. The touch device 13 allows the user to control the output of fragrance, sound, and light individually. The touch device 13 can be a touch panel, for example, a touch sensor. According to a preferred embodiment, the sound receiving device 44 is disposed on the touch device 13 for saving the space of the lid 11.

The present embodiment further comprises a power device 50 disposed below the housing 12. According to a preferred embodiment, the power device 50 is disposed in a third opening 125 of the housing and supports the weight of the smart speaker with fragrance dispenser 1. The power device 50 is connected electrically with the processor 42 for supplying power or inputting or outputting an external signal 428 such as a music file. Then the processor 42 connected electrically with the power device 50 transmits power or the external signal 428 to respective devices. The details will not be described further. According to a preferred embodiment, the power device 50 is connected electrically to the mains electricity for supplying electricity and to the Internet or remote devices for providing data output or input. In addition, the processor 42 can input or output the external signal 429 for controlling external devices through electrical connection to the power device 50. Alternatively, the processor 42 can connect to external devices wirelessly. Besides, the external devices can be controlled by voice assistants such as Alexa by Amazon or Google assistant. The external devices can be home appliances such as lamps or TVs. For example, the present invention can be applied to controlling turning on or off a TV.

Figure 5A:
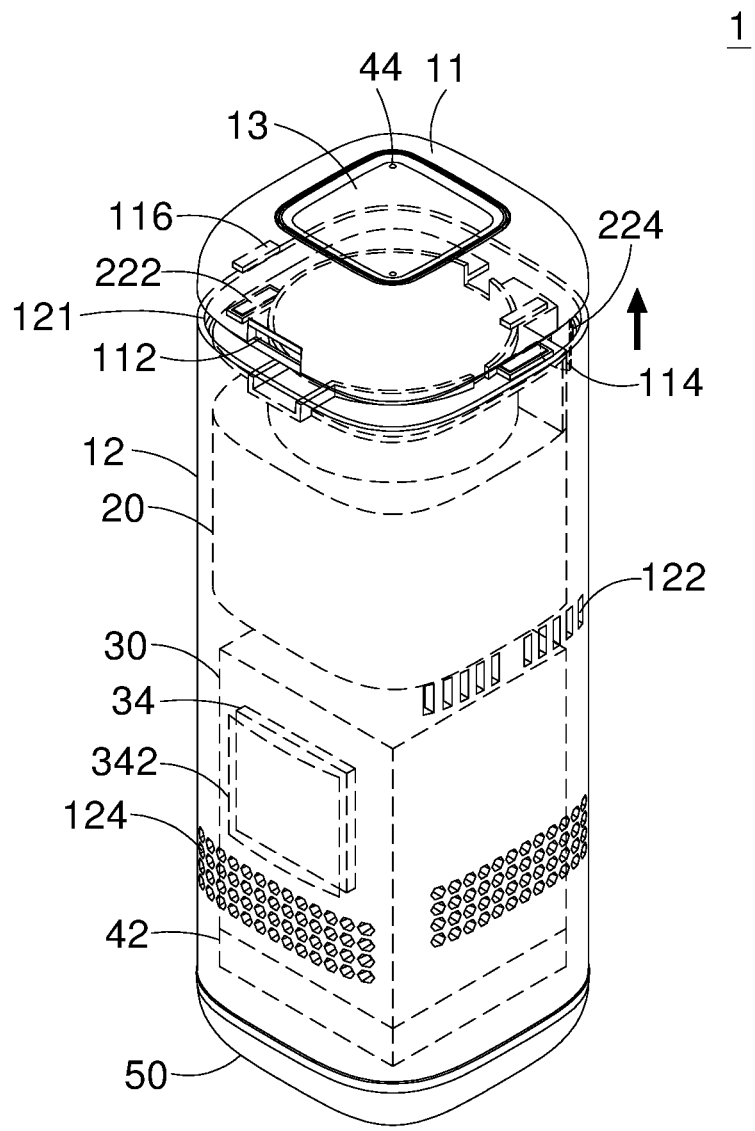
FIG. 5A and FIG. 5B show schematic diagrams of the action of the lid according to an embodiment of the present invention.
Figure 5B:
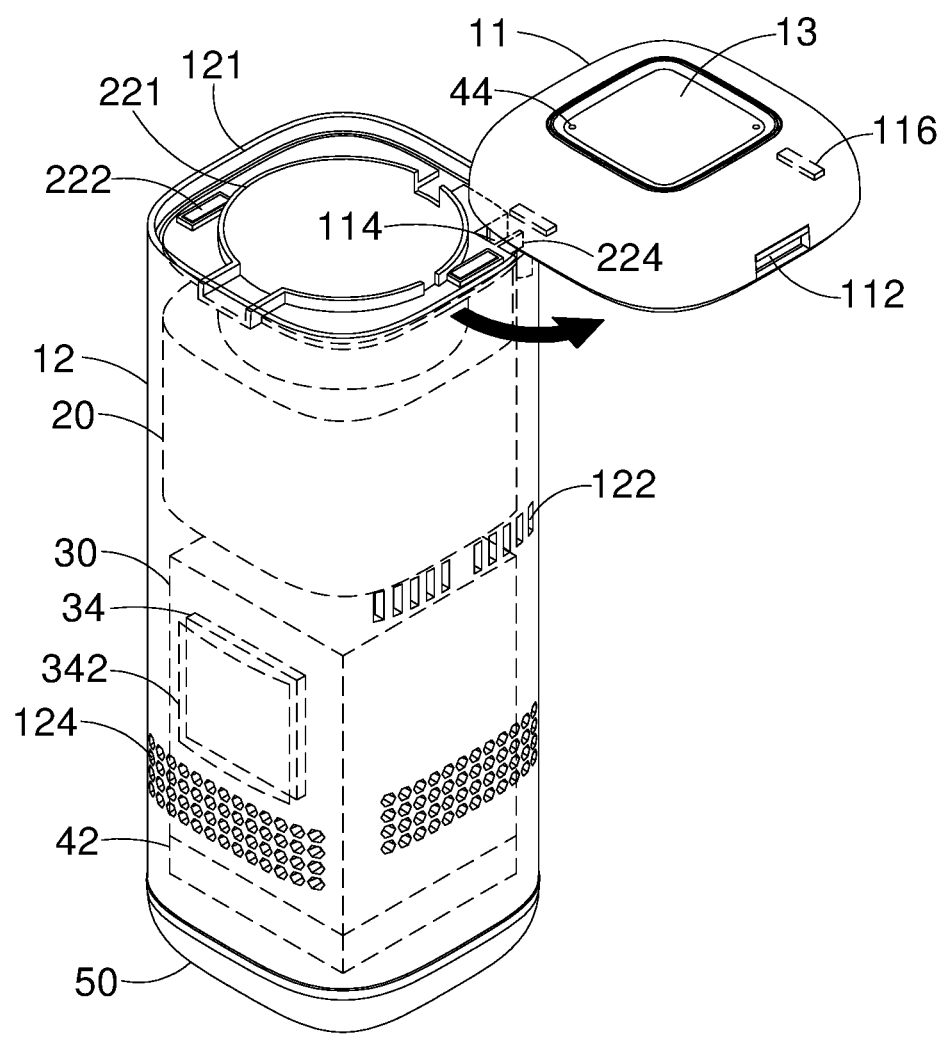

Please refer to FIG. 5A and FIG. 5B, which show schematic diagrams of the action of the lid according to an embodiment of the present invention. As shown in the figures, the present embodiment is based on the first embodiment as described above. Furthermore, a shaft 114 and one or more first magnetic member 116 are disposed below the lid 11. In addition, one or more second magnetic member 222 is disposed on the accommodating space 22 of the fragrance module 20. The location of the one or more magnetic member 116 corresponds to the location of the one or more second magnetic member 222, so that the one or more magnetic member 116 mutually attract the one or more second magnetic member 222 magnetically and thus fixing the lid 11. The accommodating space 22 includes a limiting member corresponding to the location of the shaft 114. The shaft 114 is disposed slidably in the limiting member 224 such that the lid 11 can rotate and slide. As shown in FIG. 5A, the lid 11 according to the present embodiment is pulled upward to dismiss the magnetic attraction between the one or more first magnetic member 116 and the one or more second magnetic member 222. Meanwhile, the limiting member 224 limits the raised distance of the lid 11 for avoiding the lid 11 from falling off. Then, as shown in FIG. 5B, by rotating the lid 11, the second opening 221 of the accommodating space 22 of the fragrance module 20 can be exposed for refilling liquid (such as flavoring essence), or cleaning or replacing the accommodating space 22. According to the present embodiment, by rotating the lid 11, the one or more first magnetic member 116 correspond to the one or more second magnetic member 222. Then, by pushing down the lid 11, the first opening 121 is shut off for avoiding foreign matters from entering.

The present embodiment further comprises a touch device 13 disposed on the lid 11 and connected electrically to the processor 42 for controlling the fragrance module 20, the speaker 30, and the dot-matrix display 34. The touch device 13 allows the user to control the output of fragrance, sound, and light individually by means of the processor 42. According to a preferred embodiment, the sound receiving device 44 is disposed on the touch device 13 for saving the space of the lid 11. The connection and operations of the other devices according to the present embodiment are identical to those according to the first embodiment as described above. Hence, the details will not be described again.

The lid 11 according to the present embodiment can prevent foreign matters from entering the housing 12 as well as facilitating replacing the internal devices inside the housing 12. Moreover, by using the magnetic members, the lid 11 seals tightly the first opening 121 of the housing 12 and the second opening 221 of the accommodating space 22 for avoiding the liquid in the accommodating space 22 from vaporization. Besides, the shaft 114 is used for preventing the lid 11 from falling off.

To sum up, the present invention provides a smart speaker with fragrance dispenser, which integrates the fragrance module, the speaker, and the dot-matrix display in the housing. The fragrance module adopts the ultrasonic oscillating device to nebulize the liquid, which is then blown by the fan for providing fragrance. The speaker and the dot-matrix display provide sound and light variations as well as displaying information. The processor is connected to the fragrance module and the speaker for controlling the output of fragrance, sound, and light and information display, and thus enhancing a user's senses of smelling, hearing, and sight. In addition, the functions as described above are integrated to a single structure; the lid is fixed by magnetic attraction for protecting the internal devices inside the housing.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A smart speaker with fragrance dispenser, comprising:
    a lid, having one or more air outlet on one side, and having a sound receiving device on the top;
    a housing, disposed below said lid, having one or more air inlet and one or more sound outlet on one side, and having a first opening on the top;
    a fragrance module, disposed on the inner side of said housing, including an accommodating space, an ultrasonic oscillating device, and a fan, said accommodating space located on one side of said one or more air outlet, said accommodating space including a second opening and a channel, said accommodating space stacked on said first opening and communicating said one or more air outlet, one end of said channel communicating said second opening, said ultrasonic oscillating device communicating the bottom of said accommodating space, and said fan disposed below said ultrasonic oscillating device and communicating the other end of said channel;
    a speaker, disposed separately from said fragrance module, located on the inner side of said housing, and the location of said speaker corresponding to the location of said one or more sound outlet;
    a dot-matrix display, disposed on one side of said speaker, and located on the inner side of said housing;
    a processor, disposed below said speaker, and connected electrically to said ultrasonic oscillating device, said fan, said speaker, said dot-matrix display, and said sound receiving device, respectively; and
    a power device, disposed below said housing, and connected electrically to said processor.

2. The smart speaker with fragrance speaker of claim 1, wherein said housing is a transparent member.

3. The smart speaker with fragrance speaker of claim 1, and further comprising a touch device, disposed on said lid, said sound receiving device disposed on said touch device, and said touch device connected electrically to said ultrasonic oscillating device and said fan.

4. The smart speaker with fragrance speaker of claim 1, wherein said dot-matrix display is a light-emitting-diode dot-matrix display.

5. The smart speaker with fragrance speaker of claim 1, wherein said fragrance module further includes a frame, disposed between said accommodating space and said speaker, and said ultrasonic oscillating device and said fan located on the inner side of said framer.

6. The smart speaker with fragrance speaker of claim 1, wherein said processor is connected with a remote device, and receives a wireless signal of said remote device and transmits a wireless signal to said remote device.

7. The smart speaker with fragrance speaker of claim 1, wherein said one or more air inlet is located on the top of said one or more sound outlet and said speaker is located below said one or more air inlet.

8. A smart speaker with fragrance dispenser, comprising:
    a lid, having one or more air outlet on one side, having a sound receiving device on the top, and having a shaft and one or more first magnetic member below;
    a housing, disposed below said lid, having one or more air inlet and one or more sound outlet on one side, and having a first opening on the top;
    a fragrance module, disposed below said lid and on the inner side of said housing, including an accommodating space, an ultrasonic oscillating device, and a fan, said accommodating space located on one side of said one or more air outlet, said accommodating space including a second opening and a channel, said accommodating space stacked on said first opening and communicating said one or more air outlet, one end of said channel communicating said second opening, said accommodating space including one or more second magnetic member on the top and corresponding to the location of said one or more first magnetic member, said accommodating space including a limiting member corresponding to the location of said shaft, said shaft disposed slidably in said limiting member, said ultrasonic oscillating device communicating the bottom of said accommodating space, and said fan disposed below said ultrasonic oscillating device and communicating the other end of said channel;

a speaker, disposed separately from said fragrance module, located on the inner side of said housing, and the location of said speaker corresponding to the location of said one or more sound outlet;

a dot-matrix display, disposed on one side of said speaker, and located on the inner side of said housing;

a processor, disposed below said speaker, and connected electrically to said ultrasonic oscillating device, said fan, said speaker, said dot-matrix display, and said sound receiving device, respectively; and a power device, disposed below said housing, and connected electrically to said processor.

9. The smart speaker with fragrance speaker of claim 8, wherein said housing is a transparent member.

10. The smart speaker with fragrance speaker of claim 8, wherein a shaft is disposed below said lid and connected pivotally on the top of said accommodating space.

11. The smart speaker with fragrance speaker of claim 8, and further comprising a touch device, disposed on said lid, said sound receiving device disposed on said touch device, and said touch device connected electrically to said ultrasonic oscillating device and said fan.

12. The smart speaker with fragrance speaker of claim 8, wherein said fragrance module further includes a frame, disposed between said accommodating space and said speaker, and said ultrasonic oscillating device and said fan located on the inner side of said framer.

13. The smart speaker with fragrance speaker of claim 8, wherein said processor is connected with a remote device, and receives a wireless signal of said remote device and transmits a wireless signal to said remote device.

14. The smart speaker with fragrance speaker of claim 8, wherein said one or more air inlet is located on the top of said one or more sound outlet and said speaker is located below said one or more air inlet.

* * * * *